US006268203B1

(12) United States Patent
Johnson et al.

(10) Patent No.: US 6,268,203 B1
(45) Date of Patent: Jul. 31, 2001

(54) BIOLOGICAL CONTROL OF PURPLE LOOSESTRIFE

(75) Inventors: David R. Johnson, St. Paul; Roger L. Becker, Maplewood; Elizabeth Jean Stamm-Katovich, Blaine; Robert Nyvall, Grand Rapids; Donald L. Wyse, Wyoming, all of MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/240,160

(22) Filed: Jan. 29, 1999

(51) Int. Cl.$^7$ ....................................................... C12N 1/14
(52) U.S. Cl. ........................................ 435/254.1; 435/243
(58) Field of Search .................................. 435/243, 254.1

(56) References Cited

U.S. PATENT DOCUMENTS

| 3,849,104 | 11/1974 | Daniel et al. . |
| 4,755,208 | 7/1988 | Riley et al. . |
| 5,296,369 | 3/1994 | Mortensen et al. . |
| 5,391,538 | 2/1995 | Heiny et al. . |
| 5,393,728 | 2/1995 | Charudattan et al. . |
| 5,510,316 | 4/1996 | Charudattan et al. . |

FOREIGN PATENT DOCUMENTS

| 93/22923 | 11/1993 | (WO) . |

OTHER PUBLICATIONS

"Biological control work", *University of Minnesota: Annual Gleanings, A Newsletter of the Department of Agoronomy and Plant Genetics*, 5–6 (1997).
"Purple loosestrife", Great Lakes Information Network web Site, (1998).
"Purple loosestrife in Western Canada", *Go for Green, The Active Living and Environment Program: Saskatchewan Naturally*, 3 pages, (1998).
"Purple loosestrife management", *U.S. Fish and Wildlife Service National Refuge System*, 2 pages, (1997).
Blossey, B., et al., "Host specificity and environmental impact of the weevil *Hylobius transversovitatus*, a biological control agent of purple loosestrife (*Lythrum salicaria*)", *Weed Science 42*, 128–133, (1994).
Blossey, B., et al., "Host specificity and environmental impact of two leaf beetles (*Galerucella calmariensis* and *G. pusilla*) for biological control of purple loosestrife (*Lythrum salicaria*)", *Weed Science 42*, 134–140, (1994).

Blossey, B., et al., "Performance of *Galerucella calmariensis* (Coleoptera: Chrysomelidae) on different North American populations of purple loosestrife.", *Environmental Entomology 26*(2), 439–445, (1997).
Dale, C., "Scientists poner Project Purple; Controlling the spread of purple loosestrife", *University of Waterloo* (Canada) *Alernatives Journal 24* (3), 8, (1998).
Friedlander, J., et al., "Biocontrol beetles target loosestrife at Montezuma refuge.", *Cornell Chronical 28* (41), 2 pages (1997).
Jamieson, L., "Biological Control of Purple Loosestrife", *B. C. Wetlands Networks News*, 3 pages, (1995).
Katovich, E.J., et al., "Influence of Nontarget Neighbors and Spray Volume on Retention and Efficacy of Triclopyr in Purple Loosestrife (*Lythrum salicaria*) ", *Weed Science*, 44, 143–147, (1996).
Katovich, E.J., et al., "Seasonal Fluctuations of Carbohydrate Levels in Roots and Crowns of Purple Loosestrife (*Lythrum salicaria*) ", *Weed Science*, 46, 540–544, (1988).
Malecki, R.A., et al., "Biological Control of Purple Loosestrife", *BioScience 43* (10), 680–686, (1993).
Morgan–Jones, G., "Concerning some species of *Microsphaeropsis*", *Can. J. Bot. 52*, 2575–2579, (1974).
Nyvall, R.F., "Fungi associated with the purple loosestrife (*Lythrum salicaria*) in Minnesota", *Mycologia*, 87 (4), 501–506, (1995).
Strefeler, M.S., et al., "Isozyme Characterization of Genetic Diversity in Minnesota Populations of Purple Loosestrife, *Lythrum salicaria* (Lythraceae) ", *American Journal of Botany*, 83(3), 265–273, (1996).
Strefeler, M.S., et al., "Isozyme Variation in Cultivars of Purple Loosestrife (*Lythrum* sp.) ", *HortScience*, 31 (2), 279–282, (1996).
Thompson, D.Q., et al., "Spread, Impact, and Control of Purple Loosestrife (*Lythrum salicari*) in North America Wetlands", *Fish and Wildlife Research 2*, 1–53, (1987).
Agrios, G. Plant Pathology. P. 332. Academic Press, San Diego, 1988.*
Farr et al. Fungi on Plants Products in the United States. PP. 966–967. APS Press. St. Paul, Minnesota, 1989.*

* cited by examiner

*Primary Examiner*—Remy Yucel
(74) *Attorney, Agent, or Firm*—Schwegman, Lundberg, Woessner & Kluth, P.A.

(57) ABSTRACT

The present invention provides a novel isolated and purified strain of Sphaeropsis sp. It further provides a mycoherbicidal composition that is effective in controlling purple loosestrife, and methods for controlling purple loosestrife.

41 Claims, No Drawings

BIOLOGICAL CONTROL OF PURPLE LOOSESTRIFE

BACKGROUND OF THE INVENTION

Purple loosestrife (*Lythrum salicaria*) is an aggressive invasive weed that forms uniform stands that replace diversified native flora, including important waterfowl food plants. Purple loosestrife forms dense stands where it destroys wetlands by reducing water flow and drying out the soil. Many wetlands in North America have major infestations of purple loosestrife. It has no natural enemies on the continent, neither native herbivores nor pathogens, that presently suppress invasive populations of purple loosestrife. Further, its growth is so dense that most wetland wildlife cannot use it as habitat. Moreover, it is not a preferred food for native animals in North America.

A number of characteristics have enabled purple loosestrife to become a problem. A single, mature plant can produce 2.5-million seeds annually. Established plants grow more than 2 meters tall with 30–50 stems forming wide crowns that dominate a plant canopy. Also, a strong rootstock serves as a storage organ providing resources for spring growth and regrowth if the above-ground shoots are destroyed. R. F. Nyvall, *Mycologia,* 87:501–506 (1995).

The U.S. Department of Natural Resources as well as most states in the U.S. have declared it a noxious weed and require that it be controlled. It is also on the Noxious Weed List in Alberta, Manitoba, and numerous municipalities in Canada. Governmental agencies have been trying to control the spread of purple loosestrife by various means including cutting it, pulling it out, spraying it with herbicides and burning it. Some of the control methods make the situation worse by killing surrounding plants so the purple loosestrife seedlings have no competition. For example, the seemingly obvious solution of pulling it up by the roots does not work. The whole root mass must be removed, causing extensive disturbance to the soil, and creating the very habitat in which this plant thrives. Also, all of the plant must be removed, because it can regenerate from a tiny piece of crown, stalk or leaf buds. Chemical herbicides such as Roundup® or Rodeo® are not desirable because they kill essentially all the wetland plants since they are not selective for purple loosestrife.

In addition to there not being acceptable chemical herbicides for purple loosestrife, environmental concerns make biological control a potentially attractive alternative to traditional methods of weed control. Biological control of purple loosestrife began in Germany in the 1960's. It was found that certain species of beetles (*Galerucella calmariensis, G. pusilla,* and *Hylobius transversovittatus*) could help control the spread of the weed. In 1991, the Canadian government approved the introduction of these predators of purple loosestrife as biological control agents. In 1992, the United States Department of Agriculture approved the release of these beetles as biological control agents in the U.S.

Unfortunately, it takes quite a long time (3–5 years) for these beetles to become established in an area, if they become established at all. Further, even if they become established in an area, they may not significantly impact purple loosestrife for at least 2–3 years because the plant is so resilient. Moreover, the beetles do not always kill the crown of the plant, so they may not consistently prevent seed production by the plants. The seed bank of purple loosestrife is viable for approximately nine years.

To date, no mycoherbicides have been developed from pathogens of purple loosestrife either in Europe or North America. In fact, disease symptoms are rarely observed in Europe and no pathogens have been isolated from purple loosestrife in Europe with the exception of a nematode Meloidogyne sp. reported to feed on roots in the former USSR. R. F. Nyvall, *Mycologia,* 87:501–506 (1995).

Thus, there remains a continuing need for a means to safely and effectively control the spread of purple loosestrife. There is further a long-felt, unresolved need to produce an herbicidal composition that can be sprayed, or similarly administered, onto purple loosestrife or other noxious weeds to selectively control the weeds in environments with mixed populations of useful plants, such as in a protected wetland.

SUMMARY OF THE INVENTION

The present invention provides a novel isolated and purified culture deposit ATCC no. PTA-223 that effects control of purple loosestrife (*Lythrum salicaria*). The culture may be isolated from cultivated plant material of the genus Lythrum. The cultivated plant material may be living plant tissue, dead plant residue or soil. The culture was deposited Jun. 15, 1999 in the American Type Culture Collection, 10801 University Blvd., Manassas, Va. 20110-2209, under the provision of the Budapest Treaty, and assigned ATCC accession number PTA-223. The culture may be mixed with or impregnated in an acceptable carrier to make an herbicidal composition. The carrier may be diatomaceous earth, alginate or clay. Further, the carrier may be a liquid. The carrier may also be an adjuvant, or alternatively, at least one adjuvant may be added to the herbicidal composition. The adjuvant may be an effective plant-tissue penetrating adjuvant. It may be water-miscible or water-dispersable. The adjuvant may be methylated seed oil. The culture of the present invention may be in the spore form. The effective amount of the culture is in the range of $1 \times 10^2$ to $1 \times 10^{12}$ spores per ml. It may be in the range of $10^4$ to $10^9$ spores per ml, or in the range of $10^5$ to $10^8$ spores per ml. The herbicidal composition may contain a germination activator, i.e., a compound or mixture of compounds that enhance spore generation. Examples of germination activators include, but are not limited to, monosaccharides, disaccharides, polysaccharides, amino acids, peptides, peptones, proteins, inorganic salts, and other solutes.

The present invention also provides a method for controlling purple loosestrife comprising applying an herbicidally effective amount of the above-described herbicidal composition onto a target purple loosestrife plant or onto the situs of a target plant (i.e., the area around the target plant). The herbicidal composition is applied at least once, but may be applied a plurality of times. Further, the method provides for the controlling of the target plant for multiple growing seasons.

DETAILED DESCRIPTION OF THE INVENTION

Lythrum cultivars were obtained from the Morden Research Station in Morden, Manitoba and independently from Behnke Nurseries in Maryland. These cultivars were propagated in the greenhouse and grown together with other cultivars and weedy lythrum in a loosestrife nursery. One of the inventors observed that some of the cultivars growing in the greenhouse were dying from what appeared to be a plant disease. The sick plants would begin to wilt, and then completely dry out and die. Most of the sick plants were of the cultivar, "Morden Gleam", which is a hybrid created from crossing the cultivar "Morden Pink" (*Lythrum* virgatum) with the native, winged loosestrife (*L. alatum*). The two species of Lythrum are different species from the weedy purple loosestrife (*L. salicaria*). Although the *L. virgatum* and *L. alatum* are distinct species, they are closely related and will occasionally cross to produce hybrids, as occurred in the creation of the hybrids "Morden Rose" and "Morden Gleam." Artificial crosses, however, made between the two species have rarely produced seed that will germinate.

The inventor gave some of the infected plant material to one of the other inventors, who isolated the pathogen from the cultivars. The inventor then took some of the original isolate, put it into culture and then sprayed it onto weedy purple loosestrife plants (*Lythrum salicaria*). The inventor was able to reisolate the fungal pathogen from the weedy purple loosestrife plants. It was also observed that weedy purple loosestrife plants developed the same symptoms as in the "Morden Gleam" plants. Therefore, even though fungal pathogen was initially isolated from a hybrid cross of two species, *L. virgatum* and *L. alatum,* it was able to infect another closely related, but distinct, species of Lythrum.

The inventors developed the herbicidal composition of the present invention that is a mixture formed by combining an effective amount of at least one isolated and purified strain of a pathogenic fungus specific for noxious weeds with a liquid agricultural carrier. The strain of fungal pathogen that was isolated from the "Morden Gleam" plant hosts is ATCC accession number PTA-223. An isolation procedure that may be employed to obtain the fungal pathogen involves surface sterilizing the infected stems or leaves in 70% ethanol for 3–5 minutes, sectioning material with a sterile scalpel, rinsing the material in sterile distilled water, and placing the tissue onto potato dextrose agar. The herbicidal composition can be used in a variety of environments to control growth of noxious weeds, such as purple loosestrife.

The novel mycoherbicide can be used effectively in diverse formulations, including the agronomically acceptable adjuvants and carriers normally employed for facilitating the dispersion of active ingredients for agriculture applications, recognizing a known fact that the dosage, formulations, mode of application of a chemical agent and other variable may affect its activity in any given application. The described mycoherbicide can be formulated as a suspension or dispersion, in aqueous or non-aqueous media, as a dust, as a wettable powder, as an emulsifiable concentrate, as a granule, or as any of several other known types of formulations, depending on the desired mode off application. These herbicide compositions can be applied as sprays, dusts, or granules directly to the plant or its situs where herbicidal activity is desired.

The subject fungal pathogen can be obtained by conventional culture techniques from the deposited culture specimens. To convert it to a form that will facilitate the preparation of the following described compositions, a slurry can be prepared that can then be dried onto a primary agronomically acceptable carrier, e.g., vermiculite, whereby the fungal pathogen is adsorbed onto the carrier. If desired, the slurry can be used as the concentrate for the herbicidal composition. The actual concentration of propagules in the formulated composition is not particularly critical, and is a function of practical consideration such as the properties of the vehicle or carrier, and the method of application. Certain spore concentrations, which are described herein, however, have been found to be preferred. For purposes of formulation and application, an "effective amount" is defined to mean any such quantity of propagules sufficient to infect the target plant and thereby induce the lesions involved in the lethal activity described herein.

The subject material described herein can be applied to a region to be treated by applying it directly to the soil as pre-emergence treatment or as post-emergence treatment to plant foliage, or it can be mixed intimately with the soil. The preferred mode of treatment is application after emergence of the plant foliage. The subject materials described herein can, for example, be applied to soil or plant foliage in amounts of from about 0.1 gallons per acre to 300 gallons per acre, wherein the composition is at a concentration of about $1\times10^4$ to about $1\times10^9$ spores per ml.

As used herein, an "herbicidally effective" amount of the fungal agent is an amount that is sufficient to control the growth of the target plant or plants. "Controlled" plant growth is intended to mean the ability of the fungus according to the present invention to infect its target plant to a degree sufficient to reduce or prevent the ability of the target weed, such as purple loosestrife, to detrimentally affect the growth of the surrounding native or desirable plants. It may kill one or more target plant in the selected area. However, "controlled" growth does not necessarily require the complete eradication of all of the target plants in an area.

Fungal Agents

The herbicidal composition of the invention is an effective herbicidal amount of at least one pathogenic fungal agent specific for noxious weeds combined with an agricultural carrier. The noxious weed may be purple loosestrife. The pathogen may be culture deposit ATCC no. PTA-223. Suitable fungal agents used alone or in combination are those plant pathogens that are host specific and capable of infecting the host plant and causing disease that interferes with the plant growth and/or reproduction. The plant pathogens are preferably those that selectively infect noxious weeds, such as purple loosestrife, without affecting other plants such as native wetland plants.

The method of isolating suitable fungal agents involves growing the fungus on potato dextrose agar for 10 days and harvesting spores by scraping the plates in sterile diluted water. Spores are then diluted to $10^6$ spores/ml, as determined by counting in a hemacytometer, and sprayed onto plants.

Suitable Carriers

The fungal agent is combined with a suitable carrier in an effective herbicidal concentration. Examples of suitable carriers include water, fertilizers, oils (petroleum or plant based), humectants, or combinations thereof. Alternatively, the agricultural carrier may be a solid, such as diatomaceous earth, alginate or clay, including granules or suspensions. Alternatively, the liquid may be modified to yield a physiological solution. Suitable physiological solution include sodium phosphate, sodium chloride, sodium acetate, sodium citrate and the like, preferably in an about 0.001–1M aqueous phosphate buffer. Other suitable physiological solutions are well known in the art and would include 0.85% sodium chloride. An effective herbicidal amount of the fungal agent is preferably $10^2$ to $10^{12}$ spores/ml, more preferably $10^4$ to $10^9$, and most preferably about $10^5$ to $10^8$ of the liquid medium.

Adjuvants and Germination Activators

An adjuvant may be added to the herbicidal composition of the present invention. The adjuvant provides for relatively low aqueous surface tension and increased plant tissue penetration. The adjuvants are also those that are water-miscible or water-dispersible, easily atomized, capable of being adequately retained on the foliage of plants, have low phytotoxicity, and result in a composition with relatively low surface tension.

The adjuvants useful in the composition of the present invention are those disclosed in *Adjuvants for Herbicides,*

Weed Science Society of America, Allen Press, Lawrence, Kans., (1982); or *A Guide to Agricultural Spray Adjuvants Used in the United States,* Rev. 5th ed., Thompson Publications, (1998), which are incorporated by reference herein. The preferred adjuvants are methylated seed oils. Other types of suitable adjuvants include ampholytic, cationic, anionic, and nonionic.

The adjuvant is dispersed in the liquid suspension containing the fungal agent, to yield the present herbicidal composition. The adjuvant is present in an effective plant tissue-penetrating amount that is preferably within the range of about 0.001% to 10% volume/volume, more preferably about 0.01% to 6% volume/volume, and most preferably about 0.1% to 4% volume/volume of the liquid suspension containing the fungal agent.

The herbicidal composition may also contain a germination activator. Examples would be monosaccharides, disaccharides, polysaccharides, amino acids, peptides, peptones, proteins, inorganic salts, and other solutes.

Methods of Forming and Using the Herbicidal Composition

The herbicidal composition is useful to control weed growth in a variety of environments, especially wetlands. These environments generally have a mixed population of plants, for example, cattail (Typha spp.), beggartick (Bidens spp.), broad-leaved arrowhead (*Sagittaria latifolia*), bulrush (Scirpus spp.) and willow (Salix spp.). The composition is effective against purple loosestrife without affecting the other wetland plants. The herbicidal composition is also suitable for application by low pressure spraying so that large areas of land may be easily treated.

The present herbicidal composition is formed by combining an effective amount of at least one strain of a fungal agent with an agricultural carrier, and optionally with an adjuvant and/or a germination activator, to form an essentially homogeneous dispersion.

After the herbicide is formulated, it is applied to the weed-infested area. The weed population includes purple loosestrife. Other wetland plants are not inhibited. The herbicidal mixture may be applied by ground spraying, aerial spraying, painting or brushing, or by hand or mechanical dispersion, including but not limited to backpack or other hand held devices, hydraulic or air nozzles, granular applicators, electrostatic applicators, controlled droplet applicators (CDA), or ultra-low volume (ULV) applicators. The herbicidal composition of the present invention is especially suitable for spraying.

The herbicidal mixture is applied in single or repeated applications until weed growth is effectively inhibited. The conditions leading to effective weed growth inhibition depend, in part, on the environment. For example, a single application of the herbicidal mixture may be sufficient or a plurality of application may be required. The herbicidal composition of the present invention can be applied to bare ground, plant litter or to plants of any age to inhibit growth and/or reproduction, including plants that have flowered or senesced. The herbicidal mixture is applied at a density sufficient to cover the area where weed growth is expected to be observed in amounts from about 0.1 gallons per acre to 300 gallons per acre, wherein the composition is at a concentration of about $1 \times 10^2$ to about $1 \times 10^{12}$ spores per ml. The concentration may be in the range of $10^4$ to $10^9$ spores per ml, or in the range of $10^5$ to $10^8$ spores per ml. Weed growth is effectively inhibited if the majority of weeds are infected with the fungal agent and exhibit symptoms of disease.

The following examples are intended to illustrate but not limit the invention.

EXAMPLE 1

Treatment of Purple Loosestrife with a Combination of a Fungal Agent and *Galerucella calmariensis*

The fungal agent deposited as ATCC PTA-223 produced in culture was applied in distilled water with a hand-pump sprayer. The spray solution was applied at a concentration of $1.3 \times 10^6$ spores/ml to weedy purple loosestrife plants in combination with the leaf defoliating beetle, *Galerucella calmariensis*. Adult beetles were placed in an un-capped vial. Vials were placed inside screen cages covering the plants. Beetles crawled out of vials and onto plants. *G. calmariensis* is an insect biological control agent currently being released in Minnesota to control purple loosestrife. Leaf feeding by the beetle may provide entry wounds for the fungal agent. After a period of eight days, the insects were removed by hand from purple loosestrife plants and the plants were evaluated for fungal disease symptoms. Stem cankers were found on plants. Ten plants were tested, and all plants with the fungal agent+$dH_2O$ had cankers and the cankers were determined to be caused by the fungal agent. On half of the plants there was no green tissue remaining.

EXAMPLE 2

Field Treatment of Purple Loosestrife with a Fungal Agent

In another experiment, the inventors sprayed purple loosestrife with the fungal agent in a wetland at the Dodge Nature Center in Mendota Heights, Minn. in late July. The fungal agent was sprayed as a liquid formulation with a backpack sprayer at a concentration of $1 \times 10^6$ spores/ml in combination with 3% Agri-Dex® which is manufactured by Helena Chemical Co., Memphis, Tenn. In one treatment, spores were obtained from plate culture and in the other treatment, spores were obtained from shake culture. Plates were prepared for potato dextrose agar and broth was prepared for potato dextrose broth. The cultures were grown at room temperature for 10 days, and shake cultures were shaken on an orbital shaker at 250 RPM. Two, 10 by 10 feet plots were sprayed for each treatment. Plants were evaluated for presence of the fungal agent in late August of that same year. The fungal agent was reisolated from purple loosestrife plants from the plate culture treatment.

EXAMPLE 3

Greenhouse Treatment of Purple Loosestrife with a Fungal Agent

A greenhouse study was conducted in which purple loosestrife seedlings were sprayed with a fungal agent in combination with different spray additives. Emery 6804 which is manufactured by Henkel, Cincinnati, Ohio, Agri-Dex® and Soydex® which is manufactured by Helena Chemical Co., Memphis, Tenn. were used at 3% v/v. Spore concentration was $1.0 \times 10^6$ spores/ml. Fungal stem cankers developed on purple loosestrife stems on all treated plants. The greatest disease severity and incidence occurred on plants treated with Emery 6804. The controls (not sprayed) did not become infected.

EXAMPLE 4

Treatment of Potted Purple Loosestrife with a Fungal Agent

In the spring, 60 perennial purple loosestrife crowns were planted in pots and allowed to grow. When shoots were from 4 to 8 inches tall, they were treated with one of the following: the fungal agent plus Emery 6804 (3% v/v); control plus Emery 6804 (3% v/v); and control (no treatment). Plants were rated for disease incidence and percent tissue necrosis after one month. At this time, half of the plants were cut and aboveground biomass measurements were obtained. These plants were then resprayed when the shoots were 4 to 8 inches in height for a total of two treatments per plant. After one month, data was collected as described above. Plants sprayed one time only were mulched and overwintered. In the following summer, aboveground biomass was determined for the overwintered plants (see Table 1).

TABLE 1

Efficacy of Microsphaeropsis spp. on purple loosestrife regrowth dry weights one year after application.

| Treatment | Dry Weight -g- |
| --- | --- |
| Control | 50.0 |
| Control + Emery 6804 | 50.7 |
| Control + Emery 6804 (2 applications) | 62.1 |
| Microsphaeropsis + Emery 6804 | 8.9 |
| Microsphaeropsis + Emery 6804 (2 applications) | 23.1 |
| LSD (0.05) | 30.5 |

Results of this experiment indicated that treated plants treated with the fungal agent showed disease symptoms and the fungus was reisolated from disease lesions. Control and control plus adjuvant treatments did not have disease symptoms. Crown regrowth, from plants treated two times in the first summer, was reduced as compared to control plants. Plants overwintered and harvested in the following summer also had statistically less significant regrowth as compared to control treatments. This was a significant result as it showed that crown growth may be impaired after treatment with the fungal agent, an important consideration when trying to control a persistent perennial plant such as purple loosestrife. Control of regrowth from the crown is critical for long-term suppression of purple loosestrife.

EXAMPLE 5

Specificity of the Fungal Agent as a Biological Control Agent

This experiment was conducted in wetlands located at Roseville Central Park, Roseville, Minn. In July, plots were sprayed with Emery 6804 at 3% v/v, and two rates of spores of the fungal agent; $1 \times 10^6$ spores/ml or $2 \times 10^6$ spores/ml. At the time of spraying plants were approximately 3 to 5 feet tall and were flowering. After one month, purple loosestrife plants were rated for disease incidence. Established purple loosestrife plants had noticeable disease lesions, Other wetland plants, such as cattail (Typha spp.), beggartick (Bidens spp.), broad-leaved arrowhead (*Sagittaria latifolia*), bulrush (Scirpus spp.) and willow (Salix spp.) that were sprayed with the mycoherbicide did not exhibit similar lesions and the fungal agent could not be isolated from these species. Seedling purple loosestrife plants were killed by treatments with the fungal agent.

In the following summer, the plots sprayed the previous summer were evaluated. Fungal lesions were found on stems of plants treated in the previous year, and on stems of new growth. When the lesions were examined, characteristic pycnidia were present containing spores of the fungal agent. This experiment showed that the fungal agent survived the winter and was able to reinfect purple loosestrife plants the following summer. This is an important attribute for a mycoherbicide used for control of purple loosestrife, as herbicide application costs are very expensive due to site inaccessibility.

All publications, patents and patent documents are incorporated by reference herein, as though individually incorporated by reference. The invention has been described with reference to various specific and preferred embodiments and techniques. However, it should be understood that many variations and modifications may be made while remaining within the scope of the invention.

What is claimed is:

1. An isolated and purified culture deposit ATCC no. PTA-223 that effects control of purple loosestrife (*Lythrum salicaria*).

2. The culture of claim 1 isolated from cultivated plant material of the genus Lythrum.

3. The strain of claim 2, wherein the cultivated plant material is living plant tissue, dead plant residue or soil.

4. An herbicidal composition comprising an effective amount of an isolated and purified culture deposit ATCC no. PTA-223 that effects control of purple loosestrife (*Lythrum salicaria*), and a carrier.

5. The herbicidal composition of claim 4, wherein the culture was isolated from cultivated plant material of the genus Lythrum.

6. The herbicidal composition of claim 5, wherein the cultivated plant material is living plant tissue, dead plant residue or soil.

7. The herbicidal composition of claim 4, wherein the carrier comprises diatomaceous earth, alginate or clay.

8. The herbicidal composition of claim 4, wherein the carrier is a liquid carrier.

9. The herbicidal composition of claim 4, wherein the carrier is an adjuvant.

10. The herbicidal composition of claim 4, further comprising at least one adjuvant.

11. The herbicidal composition of claim 10, wherein at least one adjuvant is an effective plant-tissue penetrating adjuvant.

12. The herbicidal composition of claim 10, wherein at least one adjuvant is water-miscible or water-dispersable.

13. The herbicidal composition of claim 10, wherein at least one adjuvant is a methylated seed oil.

14. The herbicidal composition of claim 4, wherein the culture is in the spore form.

15. The herbicidal composition of claim 14, wherein the effective amount of the culture is in the range of about $1 \times 10^2$ to about $1 \times 10^{12}$ spores per ml.

16. The herbicidal composition of claim 14, wherein the effective amount of the culture is in the range of about $1 \times 10^4$ to about $1 \times 10^9$ spores per ml.

17. The herbicidal composition of claim 14, wherein the effective amount of the culture is in the range of about $1 \times 10^5$ to about $1 \times 10^8$ spores per ml.

18. The herbicidal composition of claim 4, further comprising a germination activator.

19. The herbicidal composition of claim 18, wherein the germination activator is a monosaccharide, disaccharide, polysaccharide, amino acid, peptide, peptone, protein, or inorganic salt.

20. A method for controlling purple loosestrife comprising applying an effective amount of a herbicidal composition onto a target plant or onto the situs of a target plant, wherein the herbicidal composition comprises an isolated and purified culture deposit ATCC no. PTA-223 that effects control of purple loosestrife (*Lythrum salicaria*), and a carrier.

21. The method of claim 20, wherein the culture was isolated from cultivated plant material of the genus Lythrum.

22. The method of claim 21, wherein the cultivated plant material is living plant tissue, dead plant residue or soil.

23. The method of claim 20, wherein the carrier comprises diatomaceous earth, alginate or clay.

24. The method of claim 20, wherein the herbicidal composition is a liquid.

25. The method of claim 20, wherein the carrier is an adjuvant.

26. The method of claim 20, wherein the herbicidal composition further comprises at least one adjuvant.

27. The method of claim 26, wherein at least one adjuvant is an effective adjuvant.

28. The method of claim 26, wherein at least one adjuvant is water-miscible or water-dispersable.

29. The method of claim 26, wherein at least one adjuvant is a methylated seed oil.

30. The method of claim 20, wherein the culture is in the spore form.

31. The method of claim 30, wherein the effective amount of the culture is in the range of about $1 \times 10^2$ to about $1 \times 10^{12}$ spores per ml.

32. The method of claim 30, wherein the effective amount of the culture is in the range of about $1 \times 10^4$ to about $1 \times 10^9$ spores per ml.

33. The method of claim 30, wherein the effective amount of the culture is in the range of about $1 \times 10^5$ to about $1 \times 10^8$ spores per ml.

34. The method of claim 19, further comprising a germination activator.

35. The method of claim 34, wherein the germination activator is a monosaccharide, disaccharide, polysaccharide, amino acid, peptide, peptone, protein, or inorganic salt.

36. The method of claim 20, wherein the herbicidal composition is applied at least once.

37. The method of claim 20 wherein the target plant is controlled for multiple growing seasons.

38. The method of claim 20, further comprising applying a plant stressing agent to the target plant.

39. The method of claim 38, wherein the plant stressing agent is an insect.

40. The method of claim 39, wherein the insect is *Galerucella calmariensis*.

41. The method of claim 39, wherein the insect is *Hylobius transversovittatus*.

* * * * *

UNITED STATES PATENT AND TRADEMARK OFFICE
CERTIFICATE OF CORRECTION

PATENT NO.    : 6,268,203 B1
DATED         : July 31, 2001
INVENTOR(S)   : Johnson et al.

It is certified that error appears in the above-identified patent and that said Letters Patent is hereby corrected as shown below:

Column 7,
Line 31, delete "treated plants" and insert -- plants --, therefor.

Column 10,
Line 7, delete "claim 19" and insert -- claim 20 --, therefor.

Signed and Sealed this

Eighteenth Day of June, 2002

*Attest:*

JAMES E. ROGAN
*Director of the United States Patent and Trademark Office*

*Attesting Officer*